United States Patent
Wang et al.

(10) Patent No.: US 8,921,121 B2
(45) Date of Patent: *Dec. 30, 2014

(54) METHODS, DEVICES, AND SYSTEMS FOR CHEMILUMINESCENCE-BASED MICROFLUIDIC CELL COUNTING

(75) Inventors: Zuankai Wang, Brooklyn, NY (US); Sau Yin Chin, Bronx, NY (US); Samuel K. Sia, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 390 days.

This patent is subject to a terminal disclaimer.

(21) Appl. No.: 12/860,623

(22) Filed: Aug. 20, 2010

(65) Prior Publication Data

US 2011/0028341 A1 Feb. 3, 2011

Related U.S. Application Data

(63) Continuation-in-part of application No. 12/594,176, filed as application No. PCT/US2008/068869 on Jun. 30, 2008, now Pat. No. 8,431,090.

(60) Provisional application No. 60/947,345, filed on Jun. 29, 2007, provisional application No. 60/947,384, filed on Jun. 29, 2007, provisional application No. 61/235,634, filed on Aug. 20, 2009.

(51) Int. Cl.
*G01N 1/10* (2006.01)
*G01N 33/558* (2006.01)
*G01N 33/563* (2006.01)
*B01L 3/00* (2006.01)
*G01N 33/543* (2006.01)
*G01N 15/14* (2006.01)
*G01N 15/00* (2006.01)

(52) U.S. Cl.
CPC .... *G01N 33/54366* (2013.01); *B01L 3/502707* (2013.01); *G01N 2015/008* (2013.01); *G01N 15/147* (2013.01); *B01L 3/502746* (2013.01); *G01N 2333/70514* (2013.01); *G01N 2333/7051* (2013.01); *G01N 2015/1486* (2013.01); *B01L 3/502761* (2013.01); *G01N 15/1484* (2013.01)
USPC .......... 436/513; 436/180; 436/514; 422/502; 422/503; 422/504; 422/505

(58) Field of Classification Search
CPC .................... B01L 3/502746; B01L 3/502707; B01L 3/502761
USPC .......... 436/513, 514, 180; 422/502, 503, 504, 422/505
See application file for complete search history.

(56) References Cited

U.S. PATENT DOCUMENTS 6,267,858 B1 * 7/2001 Parce et al. .................... 204/600
6,432,630 B1 * 8/2002 Blankenstein .................... 435/4
(Continued)

FOREIGN PATENT DOCUMENTS

WO      WO 2009/006456        1/2009

OTHER PUBLICATIONS

Andersson H. et al., "Micromachined Flow-Through Filter-Chamber for Chemical Reactions on Beads," Sensors and Actuators B-Chemical (2000), vol. 67, Issues 1-2: pp. 203-208.

(Continued)

*Primary Examiner* — Bao Thuy L Nguyen
*Assistant Examiner* — Gary E Hollinden
(74) *Attorney, Agent, or Firm* — Miles & Stockbridge P.C.; Mark A. Catan (57) ABSTRACT

A chemiluminescence-based detection system and method for counting blood cells by capturing and isolating target blood cells flowing through a microfluidic chip and detecting light emitted by the captured target blood cells.

16 Claims, 4 Drawing Sheets

(56) References Cited

U.S. PATENT DOCUMENTS

| | | | |
|---|---|---|---|
| 6,540,895 B1* | 4/2003 | Spence et al. | 204/450 |
| 6,632,619 B1* | 10/2003 | Harrison et al. | 435/7.2 |
| 6,632,652 B1* | 10/2003 | Austin et al. | 435/287.2 |
| 6,767,706 B2 | 7/2004 | Quake et al. | |
| 6,936,167 B2* | 8/2005 | Hobbs et al. | 210/198.2 |
| 6,942,771 B1* | 9/2005 | Kayyem | 204/409 |
| 7,157,049 B2* | 1/2007 | Valencia et al. | 422/68.1 |
| 7,312,085 B2* | 12/2007 | Chou et al. | 436/43 |
| 7,422,669 B2* | 9/2008 | Jacobson et al. | 204/451 |
| 7,452,725 B2* | 11/2008 | Leary et al. | 436/63 |
| 8,008,032 B2* | 8/2011 | Forsyth et al. | 435/7.23 |
| 8,071,051 B2* | 12/2011 | Padmanabhan et al. | 422/502 |
| 8,071,054 B2* | 12/2011 | Oh et al. | 422/527 |
| 8,168,139 B2* | 5/2012 | Manger et al. | 422/503 |
| 8,431,090 B2* | 4/2013 | Cheung et al. | 422/503 |
| 8,435,465 B2* | 5/2013 | Sundaram et al. | 422/554 |
| 8,540,946 B2* | 9/2013 | Padmanabhan et al. | 422/502 |
| 8,541,227 B2* | 9/2013 | Christensen et al. | 435/287.9 |
| 8,613,889 B2* | 12/2013 | Pollack et al. | 422/68.1 |
| 8,658,418 B2* | 2/2014 | Daridon | 435/288.5 |
| 8,691,151 B2* | 4/2014 | Kovac et al. | 422/73 |
| 2002/0076825 A1* | 6/2002 | Cheng et al. | 436/174 |
| 2004/0229349 A1* | 11/2004 | Daridon | 435/305.2 |
| 2004/0253744 A1* | 12/2004 | Rife et al. | 436/514 |
| 2005/0136548 A1 | 6/2005 | McDevitt et al. | |
| 2007/0077605 A1 | 4/2007 | Hurt et al. | |
| 2007/0298433 A1 | 12/2007 | Sia et al. | |
| 2008/0241962 A1* | 10/2008 | Wang | 436/514 |

OTHER PUBLICATIONS

Bi XQ et al., "Modified Dynabeads Method for Enumerating CD4+ T-Lymphocyte Count for Widespread Use in Resource-Limited Situations", Jaids—Journal of Acquired Immune Deficiency Syndromes (2005), vol. 38: pp. 1-4.

Chin C. et al., Lab-on-a-chip devices for Global Health: Past Studies and Future Opportunities. Lab Chip (2007), January 7(1): pp. 41-57.

Kannangai R. et al., "Peripheral CD4 + /CD8 + T-Lymphocyte Counts Estimated by an Immunocounter Method in the Normal Healthy South Indian Adults and HIV Seropositive Individuals", J Clin Virol (2000) 17: pp. 101-108.

Mishra NN et al., "On-Chip Micro-Biosensor for the Detection of Human CD4+ Cells Based on AC Impedance and Optical Analysis", Biosens Bioelectron (2005), vol. 21: pp. 696-704.

Oleschuk RD et al., "Trapping of Bead-Based Reagents within Microfluidic Systems: On-Chip Solid-Phase Extraction and Electrochromatography", Analytical Chemistry (2000), 72: pp. 585-590.

Pattanapanyasat K. et al., "CD4+ T Cell Count as a Tool to Monitor HIV Progression & Anti-Retroviral Therapy", Indian Journal of Medical Research (2005), 121: pp. 539-549.

Sato K. et al., "Integration of an Immunosorbent Assay System: Analysis of Secretory Human Immunoglobulin A on Polystyrene Beads in a Microchip", Analytical Chemistry (2000), 72: pp. 1144-1147.

Unger et al., "Monolithic Microfabricated Valves and Pumps by Multilayer Soft Lithography," *Science,* 2000, 288(5463):113-116.

Wang C. et al., "Integration of Immobilized Trypsin Bead Beds for Protein Digestion within a Microfluidic Chip Incorporating Capillary Electrophoresis Separations and an Electrospray Mass Spectrometry Interface", Rapid Communications in Mass Spectrometry (2000), 14: pp. 1377-1383.

Balakrishnan, P. et al., "An Inexpensive, Simple, and Manual Method of CD4 T-Cell Quantitation in HIV-Infected Individuals for Use in Developing Countries", Jaids—Journal of Acquired Immune Deficiency Syndromes (2004), vol. 36, 5: pp. 1006-1010.

Ceriotti, L. et al., "An Integrated Fritless Column for On-Chip Capillary Electrochromatography with Conventional Stationary Phases," Analytical Chemistry (2002), 74: pp. 639-647.

Cheng, X. et al., "A Microfluidic Device for Practical Label-Free CD4(+) T Cell Counting of HIV-Infected Subjects," Lab on a Chip, Feb. 2007, 7(2):170-178.

Li, JJ. et al., "Application of Microfluidic Devices to Proteomics Research—Identification of Trace-Level Protein Digests and Affinity Capture of Target Peptides," Molecular & Cellular Proteomics(2002) pp. 157-168.

Mandy, F.F. et al., "Guidelines for Performing Single Platform Absolute CD4+ T-Cell Determinations with CD45 Gating for Persons Infected with Human Immunodeficiency Virus," Centers for Disease Control and Prevention. MMWR Recomm Rep (2003), vol. 52: pp. 1-18.

Mwaba, P. et al., "Use of Dried Whole Blood Spots to Measure CD4+ Lymphocyte Counts in HIV-1-Infected Patients," Lancet (2003) 362: pp. 1459-1460.

Rodriguez, W.R. et al., "A Microchip CD4 Counting Method for HIV Monitoring in Resource-Poor Settings," *PLoS Medicine,* Jul. 2005, 2(7):663-672.

Shapiro, H.M. et al., "Dried Blood Spot Technology for CD4+ T-Cell Counting," Lancet (2004), 363: pp. 164-165.

Yakovleva, J. et al., "Microfluidic Enzyme Immunoassay Using Silicon Microchip with Immobilized Antibodies and Chemiluminescence Detection", Anal. Chem. 2002, 74, 2994-3004.

Bhattacharyya et al., "Design and Testing of a Disposable Microfluidic Chemiluminescent Immunoassay for Disease Biomarkers in Human Serum Samples," Biomedical Microdevices, 2007, 9:pp. 245-251.

Lv et al., "Chemiluminescence Microfluidic System Sensor on a Chip for Determination of Glucose in Human Serum with Immobilized Reagents," Talanta, 2003, 59:pp. 571-576.

Xiang et al., "Miniaturized Immunoassay Microfluidic System with Electrokinetic Control," Biosensors and Bioelectronics, Apr. 2006, 21(1):pp. 2006-2009.

* cited by examiner

METHODS, DEVICES, AND SYSTEMS FOR CHEMILUMINESCENCE-BASED MICROFLUIDIC CELL COUNTING

CROSS-REFERENCE TO RELATED APPLICATIONS

This application claims the benefit of U.S. Provisional Application 61/235,634, filed on Aug. 20, 2009 and is a continuation-in-part of U.S. patent application Ser. No. 12/594,176, filed Sep. 30, 2009, which is a 371 of International Application No. PCT/US08/068869, filed Jun. 30, 2008, which claims the benefit of U.S. Provisional Application No. 60/947,345, filed Jun. 29, 2007, and U.S. Provisional Application No. 60/947,384, filed Jun. 29, 2007. All of the foregoing applications are hereby incorporated by reference as if set forth in their entireties herein.

BACKGROUND

Management of the human immunodeficiency virus/acquired immune deficiency syndrome (HIV/AIDS) pandemic is one of the biggest medical and clinical challenges, in both developed and developing countries. Globally, over 40 million people are now living with HIV. In the management of HIV-infected subjects, absolute counts of CD4+ T cells per micro-liter of blood have been proven to be an essential biological indicator for HIV staging and treatment decisions. The immune system needs CD4 cells to function properly. The more CD4 cells in circulation, the stronger the immune system. Clinically, a CD4 count below 200 cells per microliter of blood establishes the diagnosis of AIDS.

Currently, the gold standard for CD4 counting is through flow cytometry. High throughput flow cytometry may not be applicable in resource-poor settings due to its demanding technical requirements and expensive costs. However, availability of portable, cheap CD4 counting using advanced technologies would increase the efficiency and accessibility of CD4 monitoring, and produce a tremendous clinical impact via timely diagnosis of new AIDS patients.

SUMMARY OF THE INVENTION

The disclosed embodiments include methods, systems, devices, and articles which may provide for particle counting based on chemoluminescence. A useful application of the disclosed technology includes an integrated microfluidic-optical system to enumerate CD4 T-lymphocyte counts for HIV point of care testing at resource-poor settings. Features relating to portability and low power consumption are described.

DETAILED DESCRIPTION OF THE EMBODIMENTS

Figure 1A:
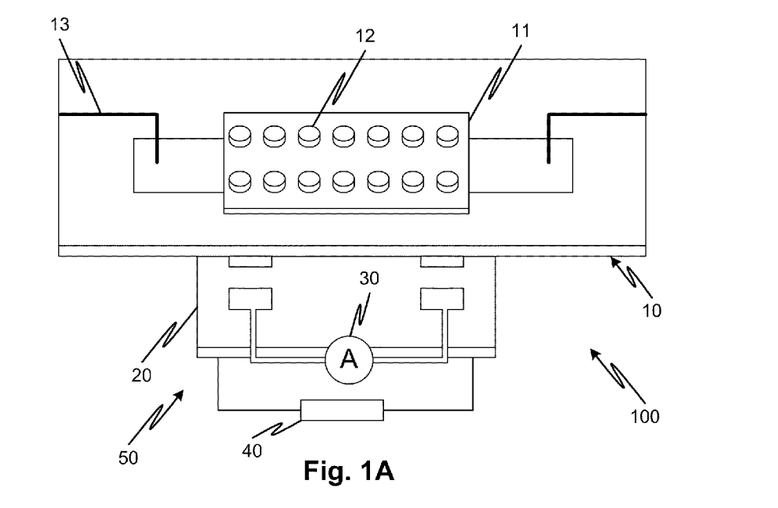
FIG. 1A is a schematic illustration of a target cell counting system according to an embodiment of the invention.

Referring to FIG. 1A, a portable integrated cell counting system 100 has a detecting module 50 positioned adjacent a microfluidic chip 10. The microfluidic chip 10 includes a flow chamber (capture chamber) 11 with a plurality of micro-channels and surface augmentations and/or a plurality of micro-trap arrays 12. The shape, size and position of the plurality of micro-channels and the plurality of micro-trap arrays are such that they collectively act as a trapping mechanism to capture and immobilize target blood cells flowing through the flow chamber 11. The trapped target cells are effectively captured and isolated from the other cells present in the blood sample flowing through the chamber 11. Whole blood, samples, washes, and reagent flowing through the microfluidic chip 10 enter the microfluidic chip through a plurality of tubes 13 and blood entry ports and spent fluids are recovered or disposed through sample exit ports (not shown). A pumping mechanism (not shown) can be employed to transfer the blood and any other samples to and from a sample source and through the microfluidic chip. The pumping mechanism can include a peristaltic pump, for example.

The detecting module 50 is positioned near the microfluidic chip 10 and adjacent the flow chamber 11 to efficiently detect and convert light emitted by the captured target blood cells. The flow chamber 11 includes a plurality of micro-channels and/or a plurality of arrayed passive hydrodynamic traps 12. The surfaces of the plurality of hydrodynamic traps (micro-traps trap arrays) 12 in the flow chamber 11 are immobilized with CD4+ antibody to allow for effective capture and isolation of CD4+ cells. The capture efficiency is over 80% from 3 pL of whole blood and the non-specific binding is maintained at a low level ranging from 3% to 15%. The detecting module 50 includes a detector 20 with suitable optics and filtering to detect light emitted by the captured target blood cells, and a source-meter 30 to convert the detected light into an electrical signal. A processor 40, which may be integrated with the detector module 50, converts the electrical signals from the source-meter 30 into a cell count. The portable system 100 can further include a microcontroller (not shown) to control the pumping mechanism, the processor 40, the detecting module 50, as well as to control sample fluid flow through the microfluidic device and to display the target cell count. Inputs from a user may be provided by suitable actuators to allow a user to operate the system 100. A housing can also be provided to form a unitary portable system. When emitted light from the target cells is generated by chemiluminescence, the detector 20 can include a chemiluminescence (CL)-based photodetector amenable to use in the portable integrated system 100.

Figure 1B:
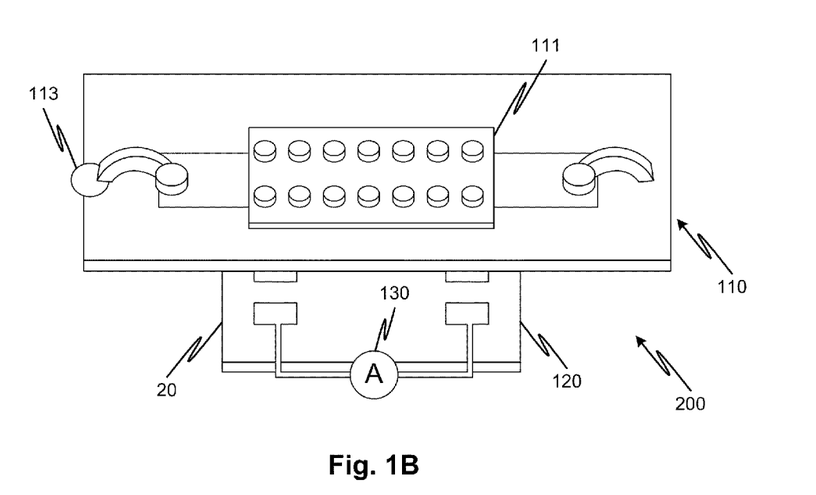
FIG. 1B is a schematic image of an integrated microfluidic-optical platform according to an embodiment of the invention.

FIG. 1B illustrates a chemiluminescence (CL)-based detection system 200 to collect and achieve a digital reading of current (proportional to CD4+ count) using a silicon photodetector 120 and a source-meter 130 in an accurate and rapid manner. Using chemiluminescence detection circumvents a limitation of the fluorescence based detection which relies on external light sources. The chemiluminescence-based detection also enables the digital reading in a rapid and automatic manner without using complex image processing and has low instrumental requirements. The system 200 includes a microfluidic chip 110 measuring approximately 30 mm×5 mm. Hydrodynamic effects and antibody immobilization can be employed to capture the target cells (cells of interest) flowing through the flow chamber 111. A hydrodynamic effect can be generated by allowing the hydrodynamic forces to transport target blood cells through the flow chamber 111 and the plurality of micro-channels and micro-trap arrays 112. Whole blood enters and exits the flow chamber 111 through tubes 113 and is transported through the flow chamber 111 using a pumping mechanism (not shown). The shape and size of the micro-channels and the micro-trap arrays 112 allows for the simultaneous transportation and immobilization of the target cells. To selectively and accurately capture target CD4 cells, CD3 antibody immobilizations and/or surface antibody-antigen interaction can also be implemented for the cell capture. Additionally, to selectively isolate CD4+ cells from the whole blood flowing through, size-based exclusion may also be employed. This approach can effectively determine CD4 absolute counts below 200 cells/µL. The technical advantages, such as, the ability to have higher capture efficiency, sensitivity and the ability to offer a digital reading on a rapid and accurate manner make it attractive for point of care diagnostics.

Figure 1C:
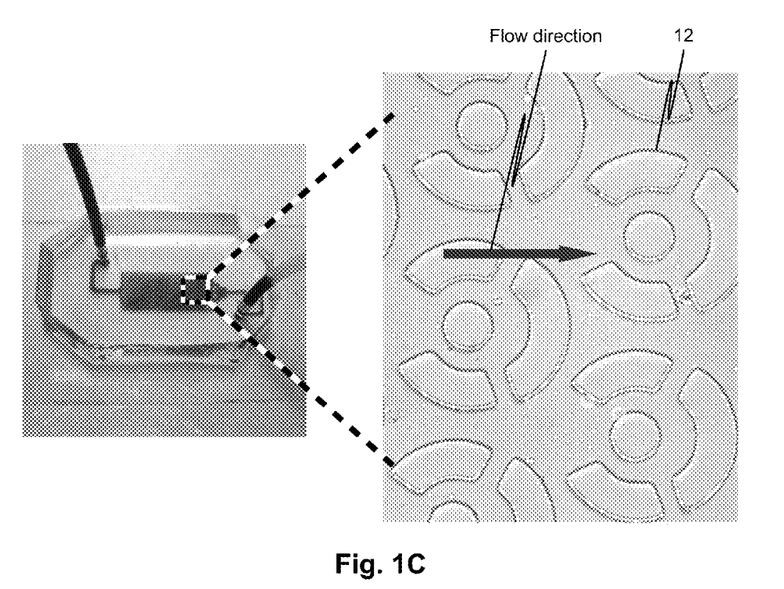
FIG. 1C is an image of a microfluidic chip filled with blood, and a magnified image of a trapping mechanism according to an embodiment of the invention.

In FIG. 1C the microfluidic chip 200 is shown filled with whole blood. A magnified image of the flow chamber (capture chamber) 111 with the plurality of micro-trap arrays 112 is also shown in FIG. 1C. The arrow indicates the direction of flow of the blood sample through the plurality of micro-trap arrays. The flow chamber 111 is approximately 10 mm×3.2 mm, and is about 45 µm tall, and it contains hundreds of micro-trap arrays 112 to significantly increase the surface area for antibody immobilization. Each micro-trap in the array 112 is designed with a pillar surrounded by C-cups with a gap of about 17.5 pm, for low non-specific binding (as shown in FIG. 1C). This space is larger than 3 pm, which was reported for effective white blood cell isolation. The distance between each trap can be approximately 25 pm and a shift of 88 pm every three rows can be introduced in the array to lead to non-linear streamlines and thereby facilitating cell contact with trap surface.

Micro-electro-mechanical systems (MEMS) technology and microfluidics may be used to integrate fluidics, mechanics, optics, and electronics on a single chip in a point of care (POC) device. Microfluidic chips maximize cell capture efficiency while minimizing non-specific binding. The microfluidics may be designed to provide flow control with low shear rates which can accommodate cells that are very sensitive to shear stress. The microfluidic chips (10, 100) may be fabricated using any suitable technique, for example, but not limited to, standard soft lithographic techniques. Using standard lithographic techniques, the chip 200 can be molded in Polydimethylsiloxane (PDMS) from a SU-8 master. One layer of 45 pm thick SU-8 3050 can be spun onto a 3 inch silicon wafer, baked, and exposed under ultraviolet (UV) light to define a negative feature of the microfluidic chip in the resist. The PDMS can be cast on the SU-8 master and baked for 2 hours in an oven having a temperature of 70° C. The PDMS can then be peeled off the mold and holes for fluidic connection can be punched. After this, PDMS chip can be bonded to glass after plasma treatment for 1 minute.

The microfluidic chips (10, 110) can be modified for maximum CD4 antibody immobilization using a method in which, after the hydroxyl groups on PDMS surface were generated after plasma treatment, the chip is immediately treated with 4% (v/v) solution of 3-mercaptopropyl trimethoxysilane ethanol for 30 minutes at room temperature so that both the PDMS and glass will be functionalized. After surface silanization, the chip can be incubated with 0.01 µmol/mL-1 GMBS (N-y-maleimidobutyryloxysuccinimide) in ethanol for 15 minutes at room temperature. NeutrAvidin can be immobilized to GMBS by incubating the chip surfaces with 10 µg ML-1 NeutrAvidin solution in PBS overnight at 4° C. Afterward, 10 µg/mL biotinylated anti-CD4 solution in PBS and 1% (w/v) BSA can be introduced to the microfluidic chip and incubated at room temperature for 15 minutes. Rinsing steps can be conducted after each step to remove unreacted molecules.

Monocyte contamination may also be reduced in both systems (100, 200) based on flow control and/or double staining. This could be a significant consideration since the presence of monocytes could artificially contribute to the total CD4+ count.

Figure 2:
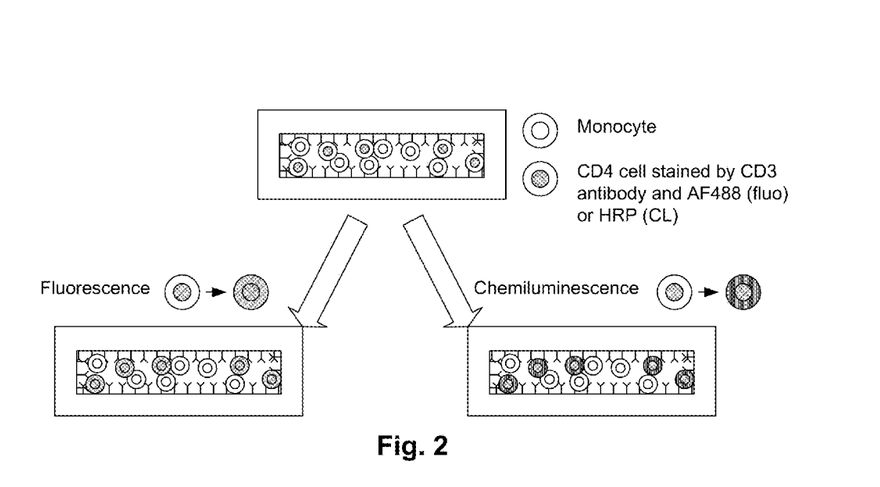
FIG. 2 is an illustration of a staining mechanism for excluding monocytes according to an embodiment of the invention.

FIG. 2 illustrates a staining mechanism for exclusion of monocyte contamination. Although monocytes might be captured on the chip, they will not be detected based on CD3 antibody staining. By coupling the captured cells to CD3 antibody conjugated with fluorophore or horseradish peroxidase (HRP), monocyte contamination exclusion may be achieved. CD3 antibody and a secondary antibody coupled with HRP may be employed to avoid staining monocytes so that monocyte contamination may be eliminated as a concern in the chemiluminescence-based detection system 200.

For blood staining, whole blood was incubated with mouse, anti-human CD3 antibodies (Invitrogen) in PBS containing 1% BSA followed by goat, anti-mouse IgG conjugated with fluorophore (AF488). For chemiluminescence (CL) based detection, goat anti-mouse IgG conjugated with HRP was used instead of IgG-AF488. The concentrations of the primary and secondary antibodies and the reaction/incubation times were optimized. Alternatively, the staining step can be done on the chip. While CD4 antigens are expressed by monocytes as well, fluorophore or HRP will not be linked to monocytes, since monocytes are not subsets of a T cell. As a result, monocytes are excluded in the counting process, though some monocyte might be captured in the microfluidic chip, as shown in FIG. 2. Normal whole blood samples could be used in the staining process. Varying CD3+/CD4+ cell counts within the range of values typically encountered in both healthy and immunocompromised individuals could be simulated by diluting blood in a PBS solution with 1% (w/v) BSA using any available and appropriate diluting methods.

In order to identify optimal flow conditions for the microfluidic chips (10, 110) fluorescence based detection can be conducted prior to cell detection. For this, after rinsing away unbound molecules in the treated microfluidic chip, stained blood is introduced into the chip and can be left for incubation on the chip for 15 minutes. A red blood cell-lysis buffer is conveyed through the flow chamber at 2 µL/min for 10 minutes to lyse red blood cells. Subsequently, PBS containing 1% BSA (w/v) is flown through the microfluidic chip at 2 pL/min for 15 minutes to rinse off unbound cells and quench the lysis buffer. In order to accurately count the CD4 cells (the particle auto-fluorescence can lead to artificially high CD4 counts), cells can be counted under a microscope at high resolution and the phase-contrast images can be compared to fluorescence images obtained, to confirm the morphology of the cell.

In order to determine the efficiency of the system (100, 200) an estimation of the capture efficiency of the system (100, 200) can be measured by estimating a ratio of the captured cells in the flow chamber (11, 111) to a cell count based on flow cytometric detection. The net count in the flow chamber can be determined by subtracting non-specific binding from the whole count. The capture efficiency of the system (100, 200) is then estimated based on the ratio of captured CD3+CD4+ cells in the flow chamber to the count obtained via flow cytometry. Flow cytometry data can be collected on a Cyromics FC 500 system, for example, using any known cytometry technique and/or protocol. In a sample experiment, a correlation coefficient (CV) of 0.93 was obtained.

Because high flow rates will lead to the captured cell shearing off while low flow rates will result in low signals, the flow rate of the system can also be optimized to minimize non-specific binding, so that the capture efficiency becomes about 80% and the non-specific binding ranges from 3% to 15%. A flow rate of about 5 µL/min was found to minimize non-specific binding. The capture efficiency can be verified based on a control experiment, in which blood samples are introduced into chips without antibody immobilized on their surfaces. In such a sample experiment, it was observed that over 70% CD4+ cells are captured on the trap surfaces. The non-specific binding of other CD3 T cells can thus be defined as background noise. The net count in the flow chamber can be determined by subtracting background from the whole count.

In operation, the integrated system (100, 200) is first assembled by closely attaching the microfluidic chip (10, 110), which could be a PDMS microchip, for example, to a photodetector (12, 120), which could be a silicon photodetector with a 1000 ms gate time, for example, for maximum optical collection. The attaching of the microfluidic chip to the photodetector is done following the incubation of blood, lysing and the rinsing steps. Prior to the chemiluminescence-based detection, dark current can also be measured ensuring that the background noise is negligible.

After the target CD4 blood cells are captured and isolated through a combination of hydrodynamic effects and antibody immobilization in the capture chamber of the microfluidic chip, a mixture of hydrogen peroxide and luminol is injected into the microfluidic chip at a flow rate of about 50 µL/min. In the presence of a catalyst, which is conjugated on the captured CD4 cell surface, the excess energy associated with the reaction between hydrogen peroxide and luminol oxygen is liberated as photons, visible as blue light (i.e., chemiluminescent emission). The emitted blue light can be collected using the silicon photodiode (50, 120) (UV818, for example) and converted to photocurrent using a source-meter (30, 130). A transient signal can be collected over a period of about 5 minutes until a large, stable negative signal is observed (corresponding to the generation of stable light). Since only captured CD3+CD4+ cells are labeled with IgG-HRP, the measured current is proportional to the CD4 cell counts.

Figure 3:
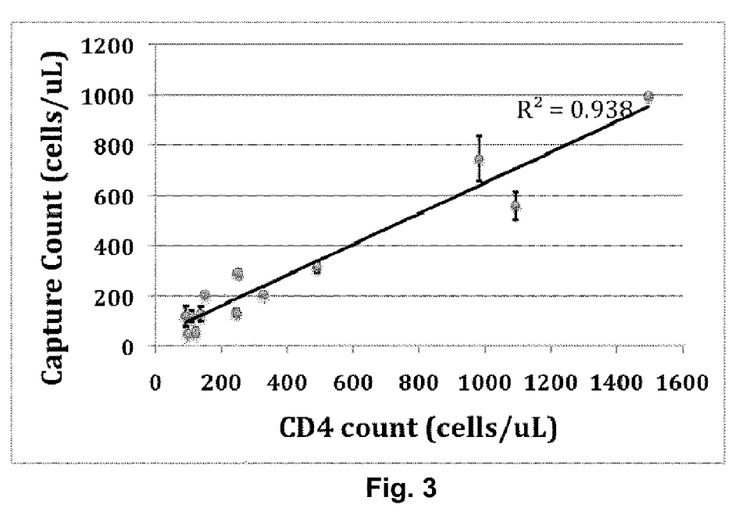
FIG. 3 is a graph illustrating captured cells versus CD4 counts according to an embodiment of the invention.

FIG. 3 illustrates a graph of data obtained using the integrated detection/counting systems as described in the embodiments of FIGS. 1A and 1B. The graph shows the number of captured cells corresponding to the true cell counts of the blood samples introduced into the chip. The correlation coefficient between the assay and standard flow cytometry was found to be 0.938. The coefficient of variation was more than 30% at high cell counts, which might be caused by cell clumping at the high end. However, CD4 Lymphocyte counts to below 200 cells/µL were measured with acceptable accuracy, indicating that the diagnostic criterion for the separation barrier between HIV and AIDS can be achieved with this approach.

Figure 4A:
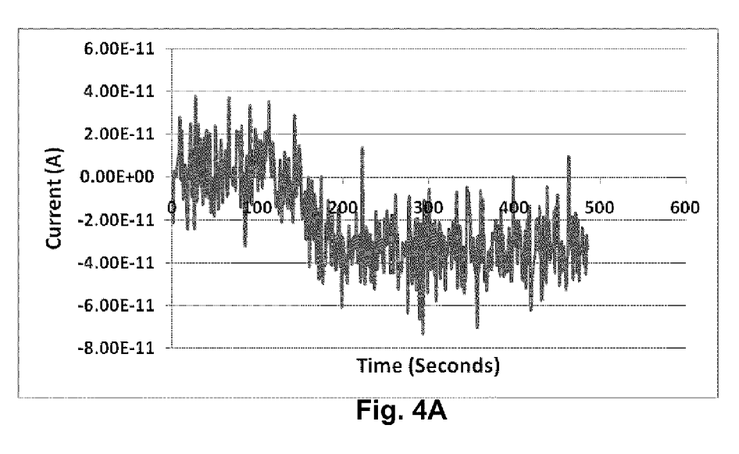
FIG. 4A is a graph illustrating a transient current generated in a chemiluminescence detection process according to an embodiment of the invention.

FIG. 4A illustrates a graph of transient current generated in a chemiluminescent detection system, and the real-time collection of current signal obtained using the integrated systems as described in the embodiments of FIGS. 1A and 1B. A stable negative signal is not developed until after 180 seconds (in the system, positive currents indicate noise). A time-average value can be calculated as a true reading and based on this statistical analysis, a quantitative current signal can be extracted with a detection level of pico-Amperes (pA). Considering that the signal at high count can reach to several hundreds of pA, the system is able to offer a wide detection range, even at very low count, for example, tens of cells. Furthermore, the detection can be finished in several minutes, which is much faster than manual counting of individual cells under a microscope, for example.

Figure 4B:
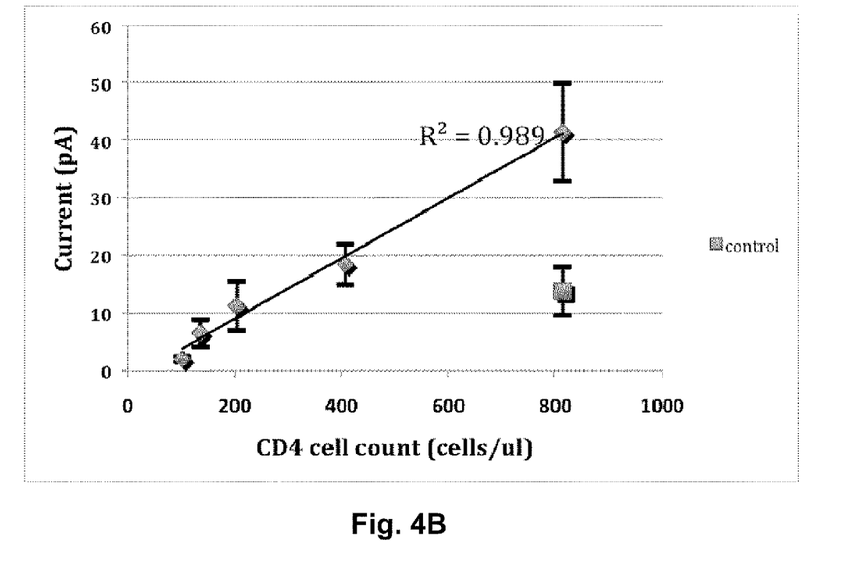
FIG. 4B is a graph illustrating a photodetector current reading corresponding to different CD4 counts according to an embodiment of the invention.

FIG. 4B shows a photodetector reading in response to different CD3+/CD4+ cell counts introduced into a microfluidic chip of a system as described in the embodiments of FIGS. 1A and 1B. FIG. 4B shows a linear relationship between measured photocurrent and cell counts, where a higher current indicates a high cell count. In an exemplary detection operation, the assay had a coefficient of variation (CV) ranging from 18% to 38%. The high CV might have been caused by the variation associated with the experimental process. If current of 25 pA is taken as a cut-off data, the device displays a sensitivity of approximately 100%, a specificity of approximately 100%.

It is therefore, apparent that there is provided, in accordance with the present disclosure, systems, devices and methods for chemiluminescence-based microfluidic cell counting. In particular, the embodiments include an integrated, portable system that can address accurate CD4 capture, isolation, and exclusion of monocyte contamination, and rapid and automatic counting of CD4+ cells. The embodiments also include further variations including the following embodiments.

Various embodiments include a cell counter comprising a light-transparent trap incorporating an immobilizer to capture target cells flowing therethrough, and a luminance detector positioned adjacent the light-transparent trap to detect light emitted by target cells immobilized by the trap. The luminance detector generates an electrical signal corresponding to a quantity of light from trapped target cells. The cell counter can further include a processing device to convert the electrical signal to a target cell count. The counter may be provided with a kit having a stain and activator capable of, upon application to target cells, causing light to be generated selectively by the target cells such that when the trapped target cells so stained are in the trap, the luminance detector generates a signal.

Various embodiments include a portable system for counting particles in a sample fluid. The system comprises a flow chamber including a trapping mechanism configured to capture and isolate target particles flowing therethrough, the trapping mechanism employing a hydrodynamic effect and an antibody immobilizer to capture and isolate the target particles, and a detecting device positioned adjacent the flow chamber and configured to detect light emitted by the trapped target particles. The detecting device is configured to generate a signal based on the detected light. The portable system further includes a processing device configured to convert said signal to a target particle count. The trapping mechanism can include a plurality of microfluidic channels with surface augmentations or a plurality of micro-trap arrays to generate said hydrodynamic effect. The system can further comprise a staining mechanism configured to stain the trapped target particles with incubated blood and an activating mechanism configured to apply an activator on the trapped target particles to generate emission of light from the trapped particles. The activating mechanism can activate fluorescence and/or chemiluminescence emission of light by the trapped target particles.

Various embodiments include an integrated blood cell counter comprising a microfluidic platform including a light-transparent trap incorporating an immobilizer to capture target blood cells flowing therethrough and a detecting system positioned adjacent said microfluidic platform to detect chemiluminescent light emitted by the captured target blood cells, and to output a blood cell count based on the detected light. The target blood cells can include CD4 blood cells. The light transparent trap can include a plurality of micro-channels with surface augmentations and the immobilizer can include an antibody or a surface antibody-antigen interaction.

Various embodiments include a chemiluminescence (CL) based detection method for counting blood cells, the method comprising capturing target blood cells flowing through an integrated microfluidic chip, the microfluidic chip including a plurality of micro-channels and an immobilizer to trap and isolate the target blood cells, generating chemiluminescence light emission from the captured target blood cells, detecting light emitted by the captured target blood cells, generating an electrical signal based on a quantity of light detected, and converting the electrical signal to a blood cell count.

Various embodiments include a method of counting particles in a sample fluid, the method comprising the step of capturing target particles flowing through a microfluidic platform, activating light emission by the captured target particles, detecting light emitted by the captured target particles, and converting a quantity of light detected to a particle count. The capturing of the target particles can employ a hydrodynamic effect and an antibody immobilization. The hydrodynamic effect can be achieved using a plurality of micro-trap arrays incorporated in the microfluidic platform.

In various embodiments the sample fluid includes blood and the target particles include CD4 blood cells. The counting method can further include staining the captured target particles before detecting the emitted light, and activating light emission by applying an activator on the captured target particles to activate one of a fluorescence emission and a chemiluminescence emission.

In various embodiments the activator includes hydrogen peroxide and luminol. In some embodiments the staining includes staining the captured target particles with incubated blood when the captured particles include CD4 blood cells.

Various embodiments include a method corresponding to the use of the above described devices and systems for counting CD4 cells. The trap may be a microfluidic channel having surface augmentation. The immobilization may be provided using antibodies. Captured cells may be coupled to CD3 antibody conjugated with either fluorophore or horseradish peroxidase (HRP). The luminance detector may include a silicon photodetector. The staining may be done by taking a sample of whole blood incubated with mouse, anti-human CD3 antibodies (Invitrogen) in PBS containing 1% BSA followed by goat, anti-mouse IgG conjugated with goat anti-mouse IgG conjugated with HRP. The staining step may be done on cells trapped in the trap.

Additional embodiments of traps, mechanisms for supplying fluid in a portable device, portable power sources, display elements and other embodiments that can be incorporated in chemiluminescent-based devices, methods, and system are described in U.S. patent application Ser. No. 12/594,176, filed Sep. 30, 2009, which is hereby incorporated by reference as if set forth in its entirety herein. For example, the incorporated application describes devices and methods for storing and delivering assay agents, pumps, control circuits, and other aspects that can readily be seen as applicable, in view of the present disclosure, to realize alternative and more detailed embodiments of a chemiluminescent-based device, systems, and methods.

Many alternatives, modifications, and variations are enabled by the present disclosure. Features of the disclosed embodiments can be combined, rearranged, omitted, etc. within the scope of the invention to produce additional embodiments.

Furthermore, certain features of the disclosed embodiments may sometimes be used to advantage without a corresponding use of other features. Accordingly, Applicant intends to embrace all such alternatives, modifications, equivalents, and variations that are within the spirit and scope of the present disclosure.

What is claimed is:

1. A portable system for counting particles in a sample fluid, comprising:
   a microfluidic chip including a flow chamber with a trapping mechanism configured to capture and isolate target particles flowing therethrough, the trapping mechanism including a plurality of microfluidic channels with surface augmentations or a plurality of micro-trap arrays, and employing a hydrodynamic effect and an immobilizer for an antibody to capture and isolate the target particles, wherein the hydrodynamic effect is generated by establishing sample fluid flow through the plurality of microfluidic channels or micro-trap arrays using a pump connected to the flow chamber;
   an activating mechanism configured to apply a chemical activator on the trapped target particles, which activator is selected to cause a material conjugated to the target particles to generate chemiluminescent light emission from the trapped target particles, whereby light is generated without the use of a light source;
   a detecting device positioned adjacent said trapping mechanism and configured to detect chemiluminescent light emitted by said trapped target particles, the detecting device generating a signal based on the detected light; and
   a processing device configured to convert said signal to a target particle count.

2. The system of claim 1, wherein the sample fluid includes blood and the target particles include blood cells and the antibody immobilizer includes a CD4+ antibody or the antibody immobilizer includes a surface antibody-antigen interaction.

3. The system of claim 1, further comprising a flow controller configured to control a flow rate of trapped target particles through the flow chamber at a predefined rate.

4. The system of claim 1, wherein the sample fluid includes blood and the target particles include CD4 blood cells and wherein the CD4 blood cells are coupled to CD3 antibody and a secondary antibody conjugated with horseradish peroxide (HRP) to effectively control monocyte contamination.

5. The system of claim 4, wherein the activating mechanism is configured to apply the activator on the trapped CD4 blood cells to generate emission of light from the trapped CD4 blood cells, wherein the activator includes hydrogen peroxide and luminol and wherein the blood is incubated with mouse, anti-human CD3 antibodies in PBS containing 1% BSA followed by goat, anti-mouse IgG conjugated with horseradish peroxide (HRP) to generate chemiluminescent light emission.

6. The system of claim 1, wherein the detecting device includes a photodetector to detect chemiluminescent light emitted by the target particles and the flow chamber further comprises sample fluid entry and exit ports and tubes, the pump being connected to establish sample fluid flow through the tubes and the sample flow chamber.

7. A method of counting particles in a sample fluid, the method comprising:

using a portable device comprising:
a microfluidic chip including a flow chamber with a trapping mechanism configured to capture and isolate target particles flowing therethrough, the trapping mechanism including a plurality of microfluidic channels with surface augmentations or a plurality of micro-trap arrays, and employing a hydrodynamic effect and an immobilizer for an antibody to capture and isolate the target particles, wherein the hydrodynamic effect is generated by establishing sample fluid flow through the plurality of microfluidic channels or micro-trap arrays using a pump connected to the flow chamber;
a detecting device positioned adjacent said trapping mechanism and configured to detect light emitted by said trapped target particles, the detecting device generating a signal based on the detected light; and
a processing device configured to convert said signal to a target particle count;
capturing target particles by trapping and isolating the target particles in the trapping mechanism;
activating chemiluminescent light emission by the captured target particles by applying a chemical activator on the captured target particles and without using an illumination source, and simultaneously blocking any sources of illumination from illuminating the captured target particles;
detecting light emitted by the captured target particles with said detecting device; and
converting a quantity of light detected to a particle count using said processing device.

8. The method of claim 7, wherein the plurality of micro-trap arrays is incorporated in a microfluidic platform and wherein the antibody immobilization further employs a surface antibody-antigen interaction.

9. The method of claim 7, wherein the sample fluid includes blood and the target particles include CD4 blood cells.

10. The method of claim 7, further comprising staining the captured target particles before detecting the emitted light.

11. The method of claim 7, wherein the activator includes hydrogen peroxide and luminol.

12. The method of claim 11, wherein staining includes staining the captured target particles with incubated blood when the captured particles include CD4 blood cells and wherein when blood is incubated with mouse, anti-human CD3 antibodies in PBS containing 1% BSA followed by goat, anti-mouse IgG conjugated with horseradish peroxide (HRP), chemiluminescent light emission is generated.

13. The method of claim 7, further comprising regulating monocyte contamination by one of controlling a flow rate of the target particles through the flow chamber and double staining.

14. A portable system for counting particles in a sample fluid, comprising:
a microfluidic chip including a flow chamber with a trapping mechanism configured to capture and isolate target particles flowing therethrough, the trapping mechanism including a plurality of microfluidic channels with surface augmentations or a plurality of micro-trap arrays, and employing a hydrodynamic effect and an immobilizer for an antibody, the antibody immobilizer including a first antibody and a second antibody conjugated to a catalyst, wherein the hydrodynamic effect is generated by establishing sample fluid flow through the plurality of microfluidic channels or micro-trap arrays using a pump connected to the flow chamber;
an activating mechanism configured to apply a chemical activator to the trapped target particles to react with the catalyst to generate chemiluminescent light emission, whereby light is generated without the use of a light source, wherein by coupling the trapped target particles to the antibody conjugated with a catalyst selectively conjugates to the target particles to the exclusion of monocytes;
a detecting device positioned adjacent said trapping mechanism and configured to detect chemiluminescent light emitted by said trapped target particles, the detecting device generating a signal based on the detected light; and
a processing device configured to convert said signal to a target particle count.

15. A method of counting particles in a sample fluid, the method comprising:
using a portable device comprising:
a microfluidic chip including a flow chamber with a trapping mechanism configured to capture and isolate target particles flowing therethrough, the trapping mechanism including a plurality of microfluidic channels with surface augmentations or a plurality of micro-trap arrays, and employing a hydrodynamic effect and an immobilizer for an antibody to capture and isolate the target particles, wherein the hydrodynamic effect is generated by establishing sample fluid flow through the plurality of microfluidic channels or micro-trap arrays using a pump connected to the flow chamber;
a detecting device positioned adjacent said trapping mechanism and configured to detect light emitted by said trapped target particles, the detecting device generating a signal based on the detected light; and
a processing device configured to convert said signal to a target particle count;
capturing target particles by trapping and isolating the target particles in the trapping mechanism;
activating chemiluminescent light emission by the captured target particles by applying a chemical activator on the captured target particles and without using an illumination source, and simultaneously blocking any sources of illumination from illuminating the captured target particles;
staining the captured target particles;
detecting light emitted by the captured target particles with said detecting device; and
converting a quantity of light detected to a particle count using said processing device,
wherein the staining of the captured target particles includes staining the captured target particles with blood incubated with CD3 antibodies, where the target particles are CD4 cells, followed by conjugation of the target particles with a catalyst for chemiluminescent light emission.

16. The method of claim 14, wherein the activator includes a mixture of hydrogen peroxide and luminol.

* * * * *